United States Patent [19]
Asano et al.

[11] Patent Number: 6,024,955
[45] Date of Patent: *Feb. 15, 2000

[54] PEPTIDES AND MONOCLONAL ANTIBODIES

[75] Inventors: Makoto Asano; Ayako Yukita; Mitsuya Hanatani; Tomoe Matsumoto; Masaji Okamoto; Hideo Suzuki, all of Ibaraki, Japan

[73] Assignee: Toagosei Co. Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/742,243

[22] Filed: Oct. 31, 1996

[30] Foreign Application Priority Data

Nov. 1, 1995 [JP] Japan .................................... 7-308184

[51] Int. Cl.$^7$ .................................................. A61K 39/395
[52] U.S. Cl. ........................... 424/130.1; 514/14; 514/15; 530/327; 530/328; 530/387.3; 530/387.7; 530/389.1; 530/389.7; 530/389.2; 530/391.1; 424/133.1; 424/138.1; 424/136.1; 424/139.1; 424/141.1; 424/145.1; 424/155.1; 424/158.1; 424/181.1
[58] Field of Search ........................ 514/14, 15; 530/327, 530/328, 387.3, 387.7, 387.9, 388.23, 388.24, 388.8, 389.1, 389.2, 389.7, 866, 391.1, 391.3, 391.7; 424/1.49, 130.1, 133.1, 138.1, 136.1, 139.1, 141.1, 145.1, 155.1, 158.1, 178.1, 181.1, 185.1, 198.1, 809

[56] References Cited

U.S. PATENT DOCUMENTS 5,569,812  10/1996  Monosov et al. ........................... 800/2

OTHER PUBLICATIONS

Osband et al, Immunology Today, vol. 11 p. 193, 1990.
Gura, Science vol. 278 p. 1041, Nov. 1997.
Dore, J.F. et al., 1987, "Metastases of human tumors in experimental animals," Anticancer Res. 7:997–1003.
Schackert, G. et al., 1989, "Unique patterns of brain metastasis produced by different human carcinomas in athymic nude mice", Int. J. Cancer 44:892–897.
Marincola, F.M. et al., 1989, "The nude mouse as a mode for the study of human pancreatic cancer," J. Surg. Res. 47:520–529.
Iwasaki, T. et al., 1997, "NG–nitro–L–arginine methyl ester inhibits bone metastasis after modified intracardiac injection of human breast cancer cells in a nude mouse model", Jpn. J. Cancer Res. 88:861–866.

Rose, D.P. et al., 1995, "Influence of diets containing ecsapenic acid on growth and metastasis of breast cancer cells in nude mice", J. Natl. Cancer Inst. 87:587–592.
Marks et al., 1995, "A novel anti–seminoma monoclonal antibody (M2A) labeled with technetium–99m: Potential application for radioimmunoscintography", Br. J. Urol. 75:225–229.
Dooley, T.P. et al., 1993, "Evaluation of a nude mouse tumor model using beta–galactosidase–expressing melanoma cells", Lab Anim. Sci. 43:48–57.
Tibbetts, L.M. et al., 1993, "Liver metastases with 10 human colon carcinoma cell line in nude mice and association with carcinoembryonic antigen production," Cancer 71:315–21.
An, Z et al., 1996, "Interferon gamma is highly effective against orthotopically–implanted human pleural adenocarcinoma in nude mice", Anticancer Res. 26:2545–2551.
Bleumenthal, R.D. et al., 1996, "Antibody penetration of tumor GS–7 xenografts in nude mice: a model for mucinous adenocarcinoma of the colon," Cancer Res. 56:3508–3515.
Velders, M.P. et al., 1995, "Immunotherapy with low and high affinity monoclonal antibodies 17–1A and 323/A3 in a nude mouse xenograft carcinoma model," Cancer Res. 55:4398–4403.
Zhu, Z. et al., 1994, "Tumor localization and therapeutic potential of an antitumor–anti–CD3 heteroconjugate antibody in human renal cell carcinoma xenograft models", Cancer Lett. 86:127–134.
Niederkorn, J.Y. et al., 1993, "Effect of anti–ganglioside antibodies on the metastatic spread of intracular melanomas in a nude mouse model of human uveal melanoma," Curr. Eye Res. 12:347–358.
Weiner, L.M. et al., 1993, "A human tumor xenograft model of therapy with a bispecific monoclonal antibody targeting c–erb–2 and CD16," Cancer Res. 53:94–100.

*Primary Examiner*—Sheela Huff
*Attorney, Agent, or Firm*—Fish & Richardson P.C.

[57] ABSTRACT

A peptide corresponding to a portion of human vascular permeability factor (VPF) and a VPF monoclonal antibody recognizing the peptide are provided. The peptide of the invention is useful as an antigen for preparing a monoclonal antibody against VPF and as a reagent for biochemical analysis. The monoclonal antibody of the invention reactive with the above peptide is useful not only as a reagent for biochemical analysis but also as a diagnostic agent or therapeutic agent for various diseases such as cancer.

25 Claims, 3 Drawing Sheets

SEQUENCE LISTING

<160> NUMBER OF SEQ ID NOS: 70

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: synthesized peptide fragment

<400> SEQUENCE: 1

Lys Pro Ser Cys Val Pro Leu Met Arg
 1               5

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: synthesized peptide fragment

<400> SEQUENCE: 2

Ser Phe Leu Gln His Asn Lys Cys Glu Cys Arg Pro
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: synthesized peptide fragment

<400> SEQUENCE: 3

Lys Cys Glu Cys Arg Pro Lys Lys Asp Arg Ala Arg
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: synthesized peptide fragment

<400> SEQUENCE: 4

Ala Pro Met Ala Glu Gly Gly Gly Gln Asn His His
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: synthesized peptide fragment

<400> SEQUENCE: 5

Met Ala Glu Gly Gly Gly Gln Asn His His Glu Val
 1               5                  10

-continued

```
<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 6

Glu Gly Gly Gly Gln Asn His His Glu Val Val Lys
      1               5                  10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 7

Gly Gly Gln Asn His His Glu Val Val Lys Phe Met
      1               5                  10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 8

Gln Asn His His Glu Val Val Lys Phe Met Asp Val
      1               5                  10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 9

His His Glu Val Val Lys Phe Met Asp Val Tyr Gln
      1               5                  10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 10

Glu Val Val Lys Phe Met Asp Val Tyr Gln Arg Ser
      1               5                  10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment
```

-continued

```
<400> SEQUENCE: 11

Val Lys Phe Met Asp Val Tyr Gln Arg Ser Tyr Cys
      1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 12

Phe Met Asp Val Tyr Gln Arg Ser Tyr Cys His Pro
      1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 13

Met Asp Val Tyr Gln Arg Ser Tyr Cys His Pro Ile
      1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 14

Asp Val Tyr Gln Arg Ser Tyr Cys His Pro Ile Glu
      1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 15

Val Tyr Gln Arg Ser Tyr Cys His Pro Ile Glu Thr
      1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 16

Tyr Gln Arg Ser Tyr Cys His Pro Ile Glu Thr Leu
      1               5                   10

<210> SEQ ID NO 17
<211> LENGTH: 12
<212> TYPE: PRT
```

```
<213> ORGANISM: Artificial Sequence
<220> FEATURE:
<223> OTHER INFORMATION: Description of Artificial Sequence: synthesized
      peptide fragment

<400> SEQUENCE: 17

Gln Arg Ser Tyr Cys His Pro Ile Glu Thr Leu Val
       1               5                  10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 18

Arg Ser Tyr Cys His Pro Ile Glu Thr Leu Val Asp
       1               5                  10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 19

Ser Tyr Cys His Pro Ile Glu Thr Leu Val Asp Ile
       1               5                  10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 20

Tyr Cys His Pro Ile Glu Thr Leu Val Asp Ile Phe
       1               5                  10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 21

His Pro Ile Glu Thr Leu Val Asp Ile Phe Gln Glu
       1               5                  10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 22

Ile Glu Thr Leu Val Asp Ile Phe Gln Glu Tyr Pro
       1               5                  10
```

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 23

Thr Leu Val Asp Ile Phe Gln Glu Tyr Pro Asp Glu
     1               5                  10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 24

Val Asp Ile Phe Gln Glu Tyr Pro Asp Glu Ile Glu
     1               5                  10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 25

Ile Phe Gln Glu Tyr Pro Asp Glu Ile Glu Tyr Ile
     1               5                  10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 26

Phe Gln Glu Tyr Pro Asp Glu Ile Glu Tyr Ile Phe
     1               5                  10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 27

Gln Glu Tyr Pro Asp Glu Ile Glu Tyr Ile Phe Lys
     1               5                  10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 28

Glu Tyr Pro Asp Glu Ile Glu Tyr Ile Phe Lys Pro
     1            5              10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 29

Tyr Pro Asp Glu Ile Glu Tyr Ile Phe Lys Pro Ser
     1            5              10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 30

Pro Asp Glu Ile Glu Tyr Ile Phe Lys Pro Ser Cys
     1            5              10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 31

Asp Glu Ile Glu Tyr Ile Phe Lys Pro Ser Cys Val
     1            5              10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 32

Glu Ile Glu Tyr Ile Phe Lys Pro Ser Cys Val Pro
     1            5              10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 33

Ile Glu Tyr Ile Phe Lys Pro Ser Cys Val Pro Leu
     1            5              10

<210> SEQ ID NO 34
<211> LENGTH: 12

```
-continued

<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 34

Tyr Ile Phe Lys Pro Ser Cys Val Pro Leu Met Arg
       1               5                  10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 35

Phe Lys Pro Ser Cys Val Pro Leu Met Arg Cys Gly
       1               5                  10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 36

Lys Pro Ser Cys Val Pro Leu Met Arg Cys Gly Gly
       1               5                  10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 37

Ser Cys Val Pro Leu Met Arg Cys Gly Gly Cys Cys
       1               5                  10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 38

Cys Val Pro Leu Met Arg Cys Gly Gly Cys Cys Asn
       1               5                  10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 39

Val Pro Leu Met Arg Cys Gly Gly Cys Cys Asn Asp
```

-continued

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 40

```
Leu Met Arg Cys Gly Gly Cys Cys Asn Asp Glu Gly
 1               5                  10
```

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 41

```
Met Arg Cys Gly Gly Cys Cys Asn Asp Glu Gly Leu
 1               5                  10
```

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 42

```
Arg Cys Gly Gly Cys Cys Asn Asp Glu Gly Leu Glu
 1               5                  10
```

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 43

```
Cys Gly Gly Cys Cys Asn Asp Glu Gly Leu Glu Cys
 1               5                  10
```

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 44

```
Gly Cys Cys Asn Asp Glu Gly Leu Glu Cys Val Pro
 1               5                  10
```

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: synthesized -continued peptide fragment

<400> SEQUENCE: 45

Cys Asn Asp Glu Gly Leu Glu Cys Val Pro Thr Glu
         1               5                  10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 46

Asp Glu Gly Leu Glu Cys Val Pro Thr Glu Glu Ser
         1               5                  10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 47

Gly Leu Glu Cys Val Pro Thr Glu Glu Ser Asn Ile
         1               5                  10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 48

Glu Cys Val Pro Thr Glu Glu Ser Asn Ile Thr Met
         1               5                  10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 49

Cys Val Pro Thr Glu Glu Ser Asn Ile Thr Met Gln
         1               5                  10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 50

Val Pro Thr Glu Glu Ser Asn Ile Thr Met Gln Ile
         1               5                  10

<210> SEQ ID NO 51

```
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 51

Thr Glu Glu Ser Asn Ile Thr Met Gln Ile Met Arg
       1               5                  10

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 52

Glu Ser Asn Ile Thr Met Gln Ile Met Arg Ile Lys
       1               5                  10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 53

Asn Ile Thr Met Gln Ile Met Arg Ile Lys Pro His
       1               5                  10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 54

Thr Met Gln Ile Met Arg Ile Lys Pro His Gln Gly
       1               5                  10

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 55

Gln Ile Met Arg Ile Lys Pro His Gln Gly Gln His
       1               5                  10

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 56
```

```
            Met Arg Ile Lys Pro His Gln Gly Gln His Ile Gly
              1               5                  10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 57

Ile Lys Pro His Gln Gly Gln His Ile Gly Glu Met
              1               5                  10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 58

Pro His Gln Gly Gln His Ile Gly Glu Met Ser Phe
              1               5                  10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 59

Gln Gly Gln His Ile Gly Glu Met Ser Phe Leu Gln
              1               5                  10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 60

Gln His Ile Gly Glu Met Ser Phe Leu Gln His Asn
              1               5                  10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 61

Ile Gly Glu Met Ser Phe Leu Gln His Asn Lys Cys
              1               5                  10

<210> SEQ ID NO 62
<211> LENGTH: 12
<212> TYPE: PRT
<213> ORGANISM: Artificial Sequence
<220> FEATURE:
```

<223> OTHER INFORMATION: Description of Artificial Sequence: synthesized
      peptide fragment

<400> SEQUENCE: 62

Glu Met Ser Phe Leu Gln His Asn Lys Cys Glu Cys
　　　　　1　　　　　　　5　　　　　　　　　　10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 63

Ser Phe Leu Gln His Asn Lys Cys Glu Cys Arg Pro
　　　　　1　　　　　　　5　　　　　　　　　　10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 64

Leu Gln His Asn Lys Cys Glu Cys Arg Pro Lys Lys
　　　　　1　　　　　　　5　　　　　　　　　　10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 65

His Asn Lys Cys Glu Cys Arg Pro Lys Lys Asp Arg
　　　　　1　　　　　　　5　　　　　　　　　　10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 66

Lys Cys Glu Cys Arg Pro Lys Lys Asp Arg Ala Arg
　　　　　1　　　　　　　5　　　　　　　　　　10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 67

Glu Cys Arg Pro Lys Lys Asp Arg Ala Arg Gln Glu
　　　　　1　　　　　　　5　　　　　　　　　　10

```
<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 68

Arg Pro Lys Lys Asp Arg Ala Arg Gln Glu Cys Asp
        1               5                  10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 69

Lys Lys Asp Arg Ala Arg Gln Glu Cys Asp Lys Pro
        1               5                  10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: synthesized
      peptide fragment

<400> SEQUENCE: 70

Asp Arg Ala Arg Gln Glu Cys Asp Lys Pro Arg Arg
        1               5                  10
```

PEPTIDES AND MONOCLONAL ANTIBODIES

BACKGROUND OF THE INVENTION

1. Field of the Invention

The present invention relates to a peptide corresponding to a partial amino acid sequence in the amino acid sequence of human vascular endothelial cell growth factor (also known as vascular permeability factor; hereinafter referred to as "VPF") and a VPF monoclonal antibody reactive with the peptide. Since this peptide is reactive with a monoclonal antibody against VPF, it is useful for the preparation of antibodies against VPF and biochemical analysis of VPF (e.g., analysis of the mode of binding of VPF to VPF receptors). Also, the VPF monoclonal antibody reactive with this peptide can be used widely for biochemical analysis of VPF and treatment of VPF-associated diseases including cancer. Thus, the present invention is useful in the fields of biochemistry, pharmacology and the like.

2. Description of the Prior Art

It is known that angiogenesis (i.e., the growth, migration and infiltration into tissues of blood capillary endothelial cells) plays important roles in physiological or pathological events including the growth of embryos, the curing of wounds and the growth of cancer cells [Folkman, J., Cancer Res. 46:467 (1986)].

As factors inducing angiogenesis, basic fibroblast growth factor (bFGF), acidic fibroblast growth factor (aFGF), vascular endothelial cell growth factor/vascular permeability factor (VEGF/VPF), platelet-derived endothelial cell growth factor (PD-ECGF) and the like are known as substances acting directly upon vascular endothelial cells, and transforming growth factor-α (TGF-α), transforming growth factor-β (TGF-β), aigiogenin, tumor necrosis factor-α (TNF-α) and the like are known as substances acting indirectly upon vascular endothelial cells [Folkman, J. & Shing, Y., J. Biol. Chem., 267:10931 (1992)].

It has been made clear that VPF is secreted in normal or tumor cell strains of mouse, rat, guinea pig, bovine and human, and that VPF exists in the brain, pituitary gland, kidney and ovary in terms of tissues [Ferrara, N., et al., Endocrine Reviews 13:18 (1992)]. Also, human VPF is reported to be involved in the angiogenesis induced by breast cancer and metastasis thereof [Weider, N. et al., N. Engl. J. Med. 324:1 (1991)]; the angiogenesis induced by renal cell carcinoma [IGAKUNO AYUMI (Progress in Medicine) 168:231 (1994)]; and the angiogenesis in retinal disorders [Adamis, A.P. et al., Biochem. Biophys. Res. Comm., 193:631 (1993)]. Further, it has been made clear that VPF transmits signals into cells by binding to receptors (Flt-1, Flk-1/KDR) present on the surface of target cells [De Vies, C. et al., Science 255:989 (1992; Terman, B. I. et al., Biochem. Biophys. Res. Commun., 187:1579 (1992)], but the mechanism of the interaction between VPF and its receptors and the mechanism of its signal transmission have not been elucidated in detail.

With respect to human VPF gene, cDNA thereof has already been isolated. The base sequence thereof and also the amino acid sequence have been determined. From this VPF gene, four proteins (of 121, 165, 189 and 206 amino acid residues, respectively) are produced and, of these proteins, the one with 121 amino acid residues (hereinafter referred to as "VPF121") and the one with 165 amino acid residues (hereinafter referred to as "VPF165") have a strong action upon vascular endothelial cells [Ferrara, N. et al., Endocrine Reviews 13: 18 (1992)]. When compared with VPF165, VPF121 has a deletion of 44 amino acid residues in the carboxyl terminal region. However, it has not been elucidated in detail whether there is any difference between VFP121 and VFP165 in the action upon vascular endothelial cells in vivo.

On the other hand, since a monoclonal antibody has higher specificity than an antiserum (polyclonal antibody) and its antigen determinant group is only one, an antibody of a required hydrophilicity can be selected and an antibody of a constantly uniform quality can be obtained. Thus, monoclonal antibodies are now widely used in biochemical analyses and clinical diagnostic procedures for various diseases. With respect to monoclonal antibodies against human VPF, a monoclonal antibody against VPF165 has already been obtained, but the site of reaction with the antibody in the above VPF is not clear [Kim, K. J. et al., Growth Factors, 7:53 (1992)].

A technology to prepare mouse monoclonal antibodies has already been established by Kohler & Milstein [Kohler & Milstein, Nature 256: 495 (1975)]. According to this technology, it is possible to prepare a monoclonal antibody against a protein, peptide, sugar, lipid or low molecular weight compound. In order to prepare a monoclonal antibody efficiently, however, the choice of an antigen to be used for immunization is very important. In other words, when a protein (high molecular weight compound) such as VPF is used as an antigen, if which amino acids are present on the surface of the antigen molecule can be made clear, it is believed that a monoclonal antibody can be prepared easily by using the amino acid sequence as an antigen because the portion of an antigen reactive with a monoclonal antibody is amino acids present on the surface of the antigen molecule.

Although the present inventors have already obtained and reported monoclonal antibodies against VPF121, further researches have been made to find out a monoclonal antibody having a stronger antitumor activity than those of the previously obtained antibodies.

OBJECTS AND SUMMARY OF THE INVENTION

It is an object of the present invention to provide a partial peptide of VPF121 which is effective in the preparation of a monoclonal antibody having a particularly excellent activity against angiogenesis-associated diseases, in particular tumors (i.e., an excellent antitumor activity) as well as a monoclonal antibody which is reactive with the above peptide and which has an excellent antitumor activity.

As a result of extensive and intensive researches toward the solution of the above assignment, the present inventors have obtained a VPF monoclonal antibody having a stronger antitumor activity than those of the previously reported monoclonal antibodies. At the same time, the inventors have found out several peptides reactive with the above-mentioned monoclonal antibody against a VPF obtained by genetic engineering techniques in 67 peptides each consisting of consecutive 12 amino acids in the amino acid sequence of VPF. In other words, the inventors have succeeded in obtaining a monoclonal antibody reactive with those specific peptides. Thus, the present invention has been achieved.

The present invention relates to a peptide having the amino acid sequence as shown in any one of SEQ ID NO: 1, SEQ ID NO: 2 or SEQ ID NO: 3.

The present invention also relates to a VPF monoclonal antibody reactive with the above peptide. As an example of such a monoclonal antibody, there is given a VPF monoclonal antibody which is reactive with the above peptide and has its isoelectric point (pI) at 5.2–5.5.

Further, the present invention relates to a pharmaceutical composition comprising as an active ingredient the VPF monoclonal antibody described above or a chimeric or humanized antibody derived therefrom.

Further, the present invention relates to a pharmaceutical composition comprising as an active ingredient a F(ab) or F(ab)'$_2$ fragment of the above-described antibody or a F(ab) or F(ab)'$_2$ fragment of a chimeric or humanized antibody derived from the above-described antibody.

Further, the present invention relates to a pharmaceutical composition comprising as an active ingredient:

(i) the above-described antibody bound to a toxin or a radioisotope;

(ii) a chimeric or humanized antibody which is derived from the above-described antibody and which is bound to a toxin or a radioisotope; or (iii) a F(ab) or F(ab)'$_2$ fragment of the above-described antibody or a F(ab) or F(ab)'$_2$ fragment of a chimeric or humanized antibody derived from the above-described antibody which fragment is bound to a toxin or a radioisotope.

Further, the present invention relates to a method for treating cancer comprising administering to a human or an animal the above-described antibody or a chimeric or humanized antibody derived therefrom.

Further, the present invention relates to a method for treating cancer comprising administering to a human or an animal a F(ab) or F(ab)'$_2$ fragment of the above-described antibody or a F(ab) or F(ab)'$_2$ fragment of a chimeric or humanized antibody derived from the above-described antibody.

Further, the present invention relates to a method for treating cancer comprising administering to a human or an animal:

(i) the above-described antibody bound to a toxin or a radioisotope;

(ii) a chimeric or humanized antibody which is derived from the above-described antibody and which is bound to a toxin or a radioisotope; or (iii) a F(ab) or F(ab)'$_2$ fragment of the above-described antibody or a F(ab) or F(ab)'$_2$ fragment of a chimeric or humanized antibody derived from the above-described antibody which fragment is bound to a toxin or a radioisotope.

DETAILED DESCRIPTION OF THE INVENTION

Figure 1:
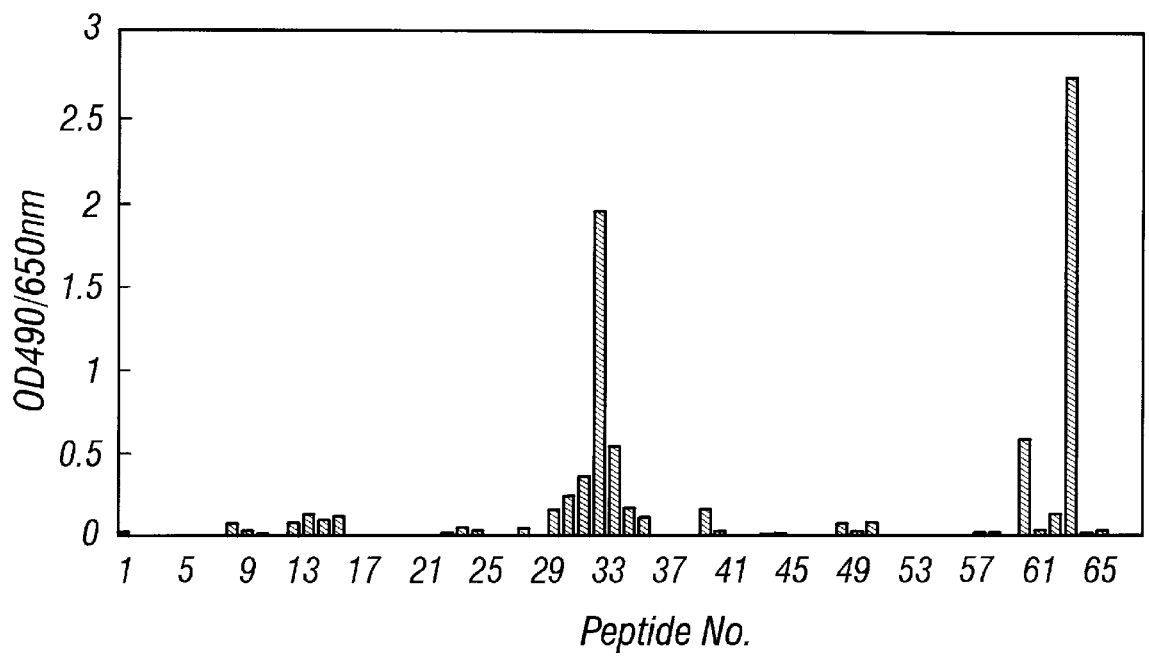
FIG. 1 is a graph showing the reactivity of MV833 antibody with 67 peptides each corresponding to a portion of human VPF121.

Hereinbelow, the present invention will be described in detail.

The peptide of the invention is able to react specifically with a VPF monoclonal antibody.

(1) Preparation of a monoclonal Antibody

A VPF monoclonal antibody may be prepared by immunizing an animal with VPF, recovering its splenic cells, fusing them with myeloma cells and culturing the resultant hybridoma cell line.

This hybridoma may be prepared according to, for example, the method of Kohler and Milstein [Nature, 256:495 (1975)].

a. Preparation of an Antibody-Producing Cell

As an animal to be immunized, rodents such as mouse, rat and rabbit may be used. As myeloma cells, mouse- or rat-derived myeloma cells may be used. Immunization is carried out by administering as an antigen 10–100 μg of VPF per animal at least 2 or 3 times at intervals of 2 to 3 weeks. The breeding of animals and the recovery of splenic cells is carried out according to conventional methods.

For the above immunization, a fusion protein obtained by fusing glutathione-S-transferase or the like to VPF or a conjugated protein obtained by binding keyhole limpet hemocyanin or the like to VPF may also be used an an antigen.

b. Preparation of Myeloma Cells

Specific examples of myeloma cells include mouse myeloma Sp2/O-Ag14 (Sp2), P3/NS1/1-Ag4-1 (NS-1) and P3-X63-Ag8-U1 cells. Subcultivation of these cells is carried out according to conventional methods.

c. Cell Fusion

Splenic cells and myeloma cells are mixed in a ratio of 1:1–1:10 and the resultant mixture is mixed with polyethylene glycol or subjected to an electric pulse treatment, to thereby achieve cell fusion.

d. Selection of a Hybridoma

The selection of fused cells (hybridoma) is carried out by culturing the cells subjected to the cell fusion in a medium containing hypoxanthine ($10^{-3}$–$10^{-5}$ M), aminopterin ($10^{-6}$–$10^{-7}$ M) and thymidine ($10^{-5}$–$10^{-6}$ M) and selecting those cells grown therein as a hybridoma.

e. Cloning of the Hybridoma

The cloning of the resultant hybridoma is repeated at least twice by the limiting dilution-culture method.

When the hybridoma is cultured similarly as conventional animal cells are cultured, the monoclonal antibody of the invention will be produced in the medium. Alternatively, the monoclonal antibody of the invention may be accumulated in a mouse ascites by transplanting the hybridoma cells into a mouse abdominal cavity and allowing them to grow.

f. Recovery and Purification of the Monoclonal Antibody

The monoclonal antibody accumulated in a culture solution of the hybridoma or an ascites is purified by a conventional method using ammonium sulfate fractionation, PEG fractionation, ion exchange chromatography and gel filtration chromatography. In some cases, affinity chromatography using protein A or protein G may also be used.

For selecting the monoclonal antibody, an enzyme immunoassay, western blotting and the like may be used. The determination of the isotype of the monoclonal antibody may be conducted by an enzyme immunoassay, the Ouchterlony method or the like.

(2) Identification of the Reaction Site of the Monoclonal Antibody a. Preparation of Peptides Each Corresponding to a Portion of the Amino Acid Sequence of VPF Sixty-seven peptides which covers the entire amino acid sequence of VPF121 are designed, each peptide consisting of 12 consecutive amino acids in the above amino acid sequence. Each of the thus designed peptides may be synthesized by, for example, the multipin peptide synthesis method [Maeji, N. J. et al., J. Immunol. Method, 134:23 (1990)].

The quantitative determination of the synthesized peptide may be conducted by determining amino groups using orthophthalaldehyde.

b. Identification of Peptides Reactive with the Monoclonal Antibody

The 67 peptide synthesized as described above cover the entire region of VPF121. Accordingly, by examining the reactivity of these peptides with the monoclonal antibody, it is possible to find out the portion of VPF with which the monoclonal antibody reacts. For the determination of reactivity, an enzyme immunoassay, the Ouchterlony method, western blotting, and the like may be used.

(3) Use of the Monoclonal Antibody as a Carcinostatic

The monoclonal antibody of the invention (including chimeric or humanized antibodies derived therefrom) may be administered to a human or an animal for the treatment of cancer. Also, antibody fragments with a lower molecular weight obtained by digesting these antibodies with an enzyme may be used for the same purpose. Further, these antibodies or antibody fragments labelled with a radioisotope (RI) or bound to a toxin may be used for the treatment or diagnosis of cancer.

In order to obtain a F(ab) or F(ab)$'_2$ fragment of the monoclonal antibody of the invention, the monoclonal antibody is treated with an enzyme such as pepsin or papain.

Specific examples of the above toxin include ricin and SAPORIN. Specific examples of the above radioisotope include indium ($^{111}$In), technetium ($^{99}$Tc), iodine ($^{131}$I, $^{125}$I), yttrium ($^{90}$Y) and rhenium ($^{186}$Re).

When the VPF monoclonal antibody of the invention or a chimeric or humanized antibody derived therefrom is administered as an carcinostatic, target diseases/disorders are not particularly limited. For example, the monoclonal antibody may be administered for specific purposes of prevention or treatment of individual carcinomas. The route of administration may be either oral (including subglossal) or parental. Parental administration includes injections, such as subcutaneous, intramuscular and intravenous injections, drip, suppositories, etc. The amount of administration varies depending on whether the subject is a human or an animal other than human, the age of the subject, the route of administration and the number of times of administration, and may be varied in a wide range. When the VPF monoclonal antibody is administered in a form of a composition comprising this antibody, an appropriate diluent and a pharmacologically acceptable carrier, the effective amount of the VPF monoclonal antibody is 0.1–100 mg/kg/day, which is administered once a day or divided into several times a day.

When the VPF monoclonal antibody of the invention is administered orally, suitable formulations such as tablets, granules, fine granules, powders, capsules, etc. usually contain conventional additives such as a binder, inclusion agent, excipient, lubricant, disintegrant, wetting agent and the like. An oral liquid formulation may take any form of an internal solution, suspension, emulsion, syrup or the like, and it may also take the form of a dry product which is re-dissolved before use. Further, the oral liquid formulation may also contain either additives or a preservative.

When a pharmaceutical composition comprising the VPF monoclonal antibody of the invention is administered parenterally, the composition contains additives such as a stabilizer, buffer, preservative, swelling agent, etc. and is provided usually in the form of an ampule containing a unit dosage, a multidose container or a tube. The above-mentioned composition may also be a powder which is re-dissolved in an appropriate carrier, such as sterilized pyrogen-free solvent, before use.

PREFERRED EMBODIMENTS OF THE INVENTION

Hereinbelow, the present invention will be described in more detail with reference to the following Examples. However, the present invention is not limited to these Examples.

EXAMPLE 1

Preparation of a Hybridoma Producing a VPF Monoclonal Antibody

A human VPF (YVPF) was purified from a culture solution of a yeast strain transformed with an isolated human VPF cDNA (Japanese Unexamined Patent Publication No. 7-31496) and a conjugate protein was prepared using keyhole limpet hemocyanin (KLH) and glutaraldehyde. Using the resultant protein as an antigen, a mouse monoclonal antibody was prepared according to conventional methods. Briefly, mouse splenic cells immunized with KLH-VPF and mouse myeloma cells (Sp2) were fused in the presence of polyethylene glycol. The resultant hybridoma was cloned by the limiting dilution-culture method. The reactivity of culture supernatants of cloned hybridomas with YVPF was examined by an enzyme immunoassay, and a hybridoma producing a monoclonal antibody reactive with YVPF was selected. The monoclonal antibody produced by this hybridoma was designated MV833. This monoclonal antibody-producing hybridoma MV833 has been deposited on Sep. 24, 1996, under the provisions of the Budapest Treaty, with the National Institute of Bioscience and Human-Technology, Agency of Industrial Science and Technology 1–3, Higashi 1-chome Tsukubashi, Ibaraki-ken, 305 Japan, under the accession No. FERM BP-5669.

EXAMPLE 2
Preparation of the VPF Monoclonal Antibody

The hybridoma as selected above was transplanted into the abdominal cavities of nude mice and their ascites containing a large quantity of the monoclonal antibody were recovered. From the resultant ascites, the monoclonal antibody was purified using a protein G affinity column (MAbTrapGII; Pharmacia). Further, the class of the monoclonal antibody was examined by an enzyme immunoassay using anti-mouse immunoglobulin subclass-specific antibodies and, as a result, the class of MV833 antibody was IgG1.

The dissociation constants of MV833 against VPF121 and VPF165, respectively, are as follows as determined by the method described below. From these results, it is understood that the monoclonal antibody of the invention has a strong affinity to VPF.

$5.7 \times 10^{-11}$ M±$0.35 \times 10^{-11}$ M (VPF121)

$1.10 \times 10^{-10}$ M±$0.11 \times 10^{-10}$ M (VPF165)

[Method for Determining Dissociation Constants]

The monoclonal antibody is prepared with 25 mM carbonate buffer (pH 9.0) containing 0.1 M sodium chloride to give a concentration of 2 μg/ml and poured into a plate with detachable wells in an amount of 100 μl/well. The plate is left at 4° C. overnight. Then, after the solution is removed from each well, 300 μl of 1% BSA-PBS is added to each well and left at 37° C. for 4 hours. After 1% BSA-PBS is removed from each well, a reaction solution containing VPF prepared with 0.1% BSA-PBS and $^{125}$I-labelled VPF ($^{125}$I-labelled VPF121 is obtained by labelling YVPF by the chloramine T method; $^{125}$I-labelled VPF165 is purchased from Amersham) is poured into the plate (200 μl/well) and left overnight. The VPF concentrations in the reaction solution are adjusted to give 0–1 ng/well for VPF121, 0–10 ng/well for VPF165 and $1 \times 10^4$ cpm/well for $^{125}$I-labelled VPF ($^{125}$I-labelled VPF121:66.7 pg/well; $^{125}$I-labelled VPF165: 116 pg/well). After the reaction solution is removed from each well, the plate is washed 6 times with 0.1% BSA-PBS. Then, each well is detached from the plate, placed in an analysis tube and subjected to counting with a γ-ray counter. Dissociation constants are determined from a scattered plot prepared from the results of the counting.

The isoelectric point (pI) of the monoclonal antibody of the invention as determined by the method described below is 5.2–5.5. The isoelectric points of other IgG1 class anti-VPF monoclonal antibodies so far reported are pI=7.0–7.5 for MV101 which the present inventors have reported and pI=4.2–5.2 for A4.6.1 of Genentech, Inc. [Kim, K. J., et al., Growth Factors, 7:53 (1992)]. Accordingly, the substance of the present invention is different from either of those substances.

[Method for Determining the Isoelectric Point]

The isoelectric focusing of the monoclonal antibody was conducted using a commercial agarose gel for isoelectric focusing (Wakamori Shokai Ltd.) on an isoelectric focusing layer available from the same manufacturer. Electrophoresis was conducted for 30 minutes at 3W with a power supply (Bio Rad) capable of generating constant electric power. After running, the gel was subjected to protein staining using a silver staining kit (Bio Rad). The isoelectric point of the monoclonal antibody was determined based on the mobility of isoelectric point marker proteins which had been electrophoresed simultaneously.

EXAMPLE 3
Identification of the Site of Reaction with the Monoclonal Antibody in VPF (a) Preparation of Peptides Each Corresponding to a Portion of the Amino Acid Sequence of VPF Sixty-seven peptides covering the entire amino acid sequence of human VPF121 were designed, each peptide consisting of 12 consecutive amino acids in the above amino acid sequence. Each peptide was synthesized by the multipin peptide synthesis [Maeji, N. J. et al., J. Immunol. Method, 134:23 (1990)].

First, the fluorenylmethoxycarbonyl (Fmoc) group was removed from 9-fluorenylmethoxycarbonyl-β-alanine introduced into the tips of pins on a pin block for 96-well assay plate with piperidine. Then, Fmoc-amino acid was condensed in the presence of dicyclohexycarbodiimide and hydroxybenzotriazole. After being washed with N,N-dimethylformamide, Fmoc-amino acid was re-condensed in the presence of dicyclohexycarbodiimide and hydroxybenzotriazole. By repeating these operations, a target peptide was synthesized. After the completion of the condensation reaction, the peptide was acetylated with acetic anhydride and the side chain protective group was removed with trifluoroacetic acid. The peptide synthesized on pins was cut out by immersing the pins in a neutral solution. The quantitative determination of the synthesized peptide was conducted by determining amino groups using orthophthalaldehyde. The amino acid sequences for the 67 peptides synthesized are shown in Table 1 (SEQ ID Nos:4–70, respectively). Figures represent peptide identification numbers.

TABLE 1

| | |
|---|---|
| 1. APMAEGGGQNHH | 35. CVPLMRCGGCCN |
| 2. MAEGGGQNHHEV | 36. VPLMRCGGCCND |
| 3. EGGGQNHHEVVK | 37. LMRCGGCCNDEG |
| 4. GGQNHHEVVKFM | 38. MRCGGCCNDEGL |
| 5. QNHHEVVKFMDV | 39. RCGGCCNDEGLE |
| 6. HHEVVKFMDVYQ | 40. CGGCCNDEGLEC |
| 7. EVVKFMDVYQRS | 41. GCCNDEGLECVP |
| 8. VKFMDVYQRSYC | 42. CNDEGLECVPTE |
| 9. FMDVYQRSYCHP | 43. DEGLECVPTEES |
| 10. MDVYQRSYCHPI | 44. GLECVPTEESNI |
| 11. DVYQRSYCHPIE | 45. ECVPTEESNITM |
| 12. VYQRSYCHPIET | 46. CVPTEESNITMQ |
| 13. YQRSYCHPIETL | 47. VPTEESNITMQI |
| 14. QRSYCHPIETLV | 48. TEESNITMQIMR |
| 15. RSYCHPIETLVD | 49. ESNITMQIMRIK |
| 16. SYCHPIETLVDI | 50. NITMQIMRIKPH |
| 17. YCHPIETLVDIF | 51. TMQIMRIKPHQG |
| 18. HPIETLVDIFQE | 52. QIMRIKPHQGQH |
| 19. IETLVDIFQEYP | 53. MRIKPHQGQHIG |
| 20. TLVDIFQEYPDE | 54. IKPHQGQHIGEM |
| 21. VDIFQEYPDEIE | 55. PHQGQHIGEMSF |
| 22. IFQEYPDEIEYI | 56. QGQHIGEMSFLQ |
| 23. FQEYPDEIEYIF | 57. QHIGEMSFLQHN |
| 24. QEYPDEIEYIFK | 58. IGEMSFLQHNKC |
| 25. EYPDEIEYIFKP | 59. EMSFLQHNKCEC |
| 26. YPDEIEYIFKPS | 60. SFLQHNKCECRP |
| 27. PDEIEYIFKPSC | 61. LQHNKCECRPKK |
| 28. DEIEYIFKPSCV | 62. HNKCECRPKKDR |
| 29. EIEYIFKPSCVP | 63. KCECRPKKDRAR |
| 30. IEYIFKPSCVPL | 64. ECRPKKDRARQE |
| 31. YIFKPSCVPLMR | 65. RPKKDRARQECD |
| 32. FKPSCVPLMRCG | 66. KKDRARQECDKP |
| 33. KPSCVPLMRCGG | 67. DRARQECDKPRR |
| 34. SCVPLMRCGGCC | |

(b) Identification of Peptides Reactive with MV833 Antibody

The 67 peptides synthesized by the above procedures correspond to the entire region of human VPF 121. Therefore, by examining the reactivity of the 67 peptides with MV833 antibody, it is possible to identify the portion of VPF with which MV833 reacts. Then, the reactivity of the 67 peptides with MV833 antibody was examined by an enzyme immunoassay. Briefly, 20 μM peptide solutions each containing one of the 67 peptides were added to a 96-well NOS plate (Coaster) and left at room temperature for 2 hours. After each well was washed with 0.1% BSA-PBS 3 times, 2% BSA-PBS was added thereto and left at room temperature for 1 hour. After the removal of 2% BSA-PBS, MV833 (in 1% BSA-PBS solution) was added to the plate and left at room temperature for 1 hour. After each well was washed with 0.1% BSA-PBS 6 times, peroxidase-labelled sheep anti-mouse IgG (Amersham) (in 0.1% BSA-PBS) was added thereto and left at room temperature for 1 hour. After each well was washed with 0.1% BSA-PBS 6 times, 0.2 M Tris-citrate buffer (pH 5.2) containing 8.3 mg/ml orthophenylenediamine dihydrochloride and 0.01% hydrogen peroxide was added for coloring. The reaction was terminated by adding 2 N sulfuric acid and then absorbance (OD490/650) was measured. The results of the measurement by the above procedures are plotted in FIG. 1.

MV833 antibody reacted strongly with 5 peptides (Identification Nos. 31, 32, 33, 60 and 63) of the 67 peptides tested. Since the peptides of Identification Nos. 31–33 commonly contain a sequence of KPSCVPLMR, it is considered that MV833 antibody is reacting with the amino acid sequence KPSCVPLMR in this region. Therefore, it is expected that MV833 antibody is reacting with the KPSCVPLMR sequence, the SFLQHNKCECRP sequence and the KCECRPKKDRAR sequence of VPF. Because it is considered that an antibody recognizes a portion exposed on the surface of a protein, the portions of the 3 amino acid sequences described above can be said to be exposed on the surface of VPF. Although it is said that the antigen determinant group of a monoclonal antibody is only one, there are some cases where an antibody recognizes an antigen three-dimensionally if the antigen is a high molecular weight substance such as a protein taking a higher-order structure, and reacts with incontinuous amino acid sequences of two or more portions when the reactivity of the antibody is examined at the primary structure level of the protein. Since MV833 antibody reacted with the amino acid sequences of 2 portions in VPF, it is considered that this antibody recognizes the amino acid sequences of 2 portions three-dimensionally and simultaneously.

In the study of an extremely small quantity of a protein or a virus, currently the cloning of the gene thereof is conducted first. Then, the amino acid sequence of the protein is predictable from the base sequence of the gene. Based on the amino acid sequence, a highly hydrophilic site is searched and a synthetic peptide for the site is prepared. Then, a polyclonal or monoclonal antibody against this peptide is prepared and used for immunological analysis. The search for a highly hydrophilic site is conducted using, for example, the method of Hoop & Woods [Proc. Natl. Acad. Sci. USA 78:3824 (1981)], but this method is not necessarily applicable to any protein. Since the present invention has identified in the site exposed on the surface of VPF those portions which are important for tumor growth, it has become possible to readily prepare a VPF antibody with a strong antitumor activity. Furthermore, the method employed in the present invention is also applicable as a method to identify the site exposed on the surface of a protein.

EXAMPLE 4

Antitumor Test of the VPF Monoclonal Antibody i) Antitumor Test against HT-1080

An antitumor test of the monoclonal antibody of the present invention was conducted as follows using the HT-1080 tumor cell line implanted in nude mice (BALB/c-nu/nu).

HT-1080 tumor cells were transplanted subcutaneously to nude mice in advance. The mice were bred until tumor masses were formed. Then, a section of about 2 mm square was cut out from the tumor mass and inoculated to another nude mouse subcutaneously in the abdominal portion. From the next day of the inoculation, the monoclonal antibody of the invention was administered intraperitoneally 9 times in the total at a dose of 25 μg/mouse/day. (The administration was conducted 1, 2, 3, 4, 7, 8, 9, 10 and 11 days after the inoculation). As control groups, one group received no monoclonal antibody and other two groups were administered monoclonal antibody MV101 and MV303, respectively, which differ from the monoclonal antibody of the invention. Each group consisted of 4 nude mice.

Figure 2:
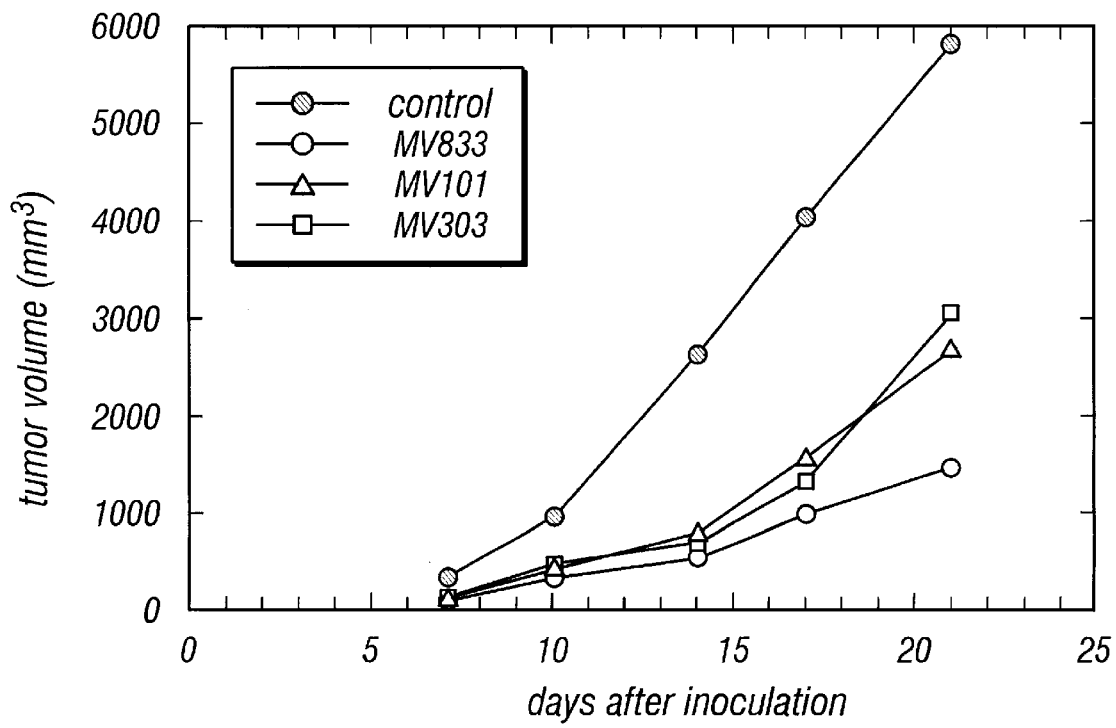
FIG. 2 is a graph showing the antitumor activity of MV833 antibody (●: MV833 antibody; ▲: MV101 antibody; ■:MV303 antibody; and ○: control).

As a result of comparison of tumor formation and the size (volume) of tumor in each group, as shown in FIG. 2, the monoclonal antibody of the invention has been proved to exhibit a superior tumor growth suppressing activity to not only the activity of the non-treated control group but also the activities of other monoclonal antibodies. In FIG. 2, mark "○" represents the non-treated control group; mark "●" represents the group which was administered MV833 antibody of the invention; marks "▲" and "■" represent those groups which were administered monoclonal antibodies (MV101 and MV303, respectively).

ii) Antitumor Spectra of the VPF Monoclonal Antibody

Each of the tumors shown in the table of antitumor spectra (Table 2) was transplanted subcutaneously to nude mice, which were bred until tumor masses were formed. Then, a section of about 2 mm square was cut out from the tumor mass and inoculated into another nude mouse subcutaneously in the abdominal portion.

The administration of the monoclonal antibody of the invention started as follows. For HT-1080, A673 or LS180-inoculated nude mice, the administration started on the next day of the inoculation. For SW480, A375, G 361, WM115, A549, PC-14, BXPC-3, ASPC-1, A431 or HeLa/v5-inoculated nude mice, the administration started 9 days after the inoculation. For PLC/PRF/5-inoculated nude mice, the administration started 10 days after the inoculation. For LoVo-inoculated nude mice, the administration started 16 days after the inoculation. The monoclonal antibody of the invention was administered intravenously every 4 days at a dose of 100 μg/mouse. The control group was administered physiological saline in a similar manner. Each group consisted of 5 nude mice.

Table 2 shows the results of comparison of the tumor volumes in the groups treated with the monoclonal antibody of the invention and the control group.

As a result of examination of the antitumor spectra of the VPF monoclonal antibody, antitumor effect was observed against all of the tumors examined.

TABLE 2

Antitumor activitiy of anti-VPF MoAb, against
various human tumors implanted in nude mice

| Cell Line (human) | | Start of injection (Days after inocculation) | T/C |
|---|---|---|---|
| HT-1080 | fibrosarcoma | 1 day | 0.22 (day 22) |
| A673 | rhabdomyosarcoma | 1 day | 0.04 (day 28) |
| LS180 | colon, adenocarcinoma | 1 day | 0.10 (day 26) |
| SW480 | colon, adenocarcinoma | 9 days | 0.10 (day 49) |
| LoVo | colon, adenocarcinoma | 16 days | 0.16 (day 35) |
| A375 | malignant melanoma | 9 days | 0.31 (day 25) |
| G361 | malignant melanoma | 9 days | 0.30 (day 49) |
| WM115 | melanoma | 9 days | 0.28 (day 49) |
| A549 | lung carcinoma | 9 days | 0.27 (day 77) |
| PC-14 | lung carcinoma | 9 days | 0.33 (day 39) |
| BXPC-3 | primary pancreatic adenocarcinoma | 9 days | 0.20 (day 25) |
| ASPC-1 | metastatic pancreatic adenocarcinoma | 9 days | 0.37 (day 63) |
| A431 | epidermoid carcinoma | 9 days | 0.30 (day 41) |
| HeLa/v5 | epidermoid carcinoma, cervix | 9 days | 0.24 (day 31) |
| PLC/PRF/5 | Hepatoma | 10 days | 0.27 (day 42) |

Dose: 100 μg/mouse, i.v.
Treatment: every four days from 1 day or 9 days or 10 days or 16 days after the inoculation.

EXAMPLE 5
Antitumor Test (Effect of a Joint Use with an Existing Carcinostatic)

Since the point of action of the monoclonal antibody is blood vessels extending to tumors, this monoclonal antibody, being completely different from conventional carcinostatics of which the target is tumor cells per se, can be used with various medicines effectively as a suppressant. It has been suggested that, with this suppressant, chemotherapy of cancers can be conducted more effectively.

Human fibrosarcoma (HT-1080) subcutaneously subcultured in nude mice was cut out in a section of about 2 mm square and inoculated subcutaneously into 6 nude mice of another group using a trocar. On the next day of the inoculation, the existing carcinostatic mitomycin (3 mg/kg) or cisplatin (5 mg/kg) was injected into the tail vein once, and the monoclonal antibody of the invention was injected into the tail vein at a dose of 12.5 μg/mouse every 4 days from the next day of the transplantation.

In those groups which received an existing carcinostatic alone, 3 or 6 mg/kg of mitomycin or 5 or 10 mg/kg of cisplatin was administered in a similar manner as employed in the joint administration groups (i.e. every 4 days into the tail vein).

In the group which received the monoclonal antibody alone, 12.5 μg/mouse of the monoclonal antibody was administered similarly (i.e. every 4 days into the tail vein).

The tumor volume of each mouse was calculated by measuring the diameter of the tumor with the passage of time. At the same time, changes in body weight were also observed.

The results are shown in FIGS. 3–6.

Figure 3:
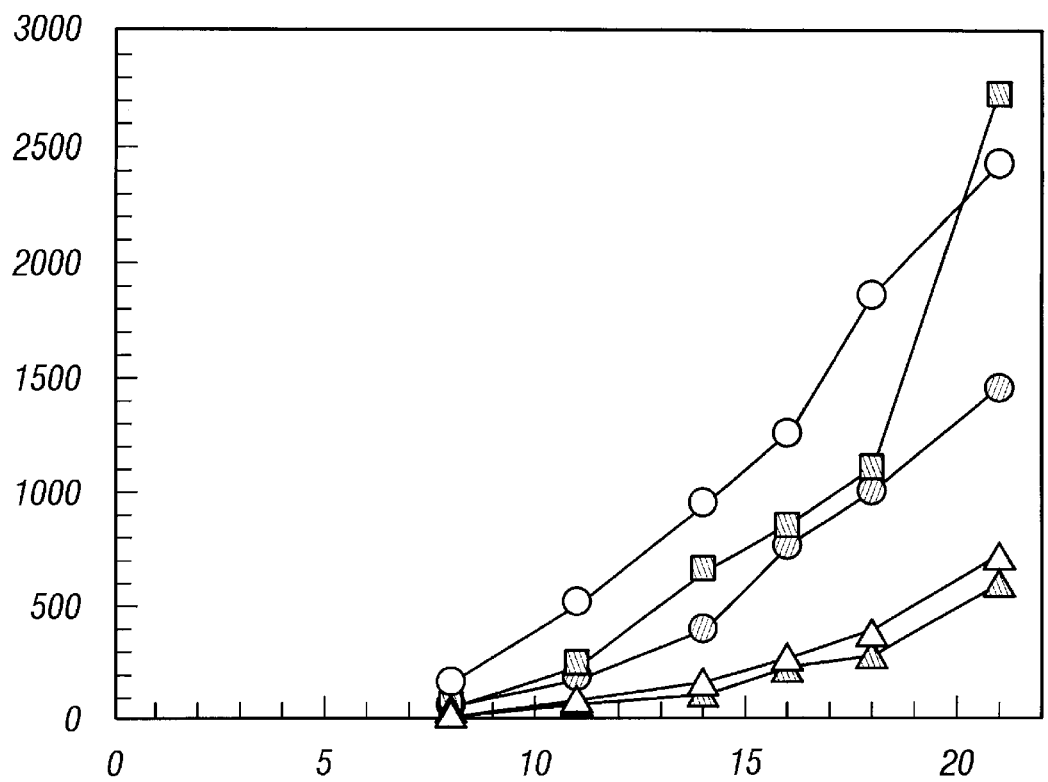
FIG. 3 is a graph showing the changes in tumor volume when the VPF monoclonal antibody and mitomycin were used jointly. In this Fig., mark "●" represents the group which was administered the monoclonal antibody alone at a dose of 12.5 μg/mouse; mark "▲" represents the group which was administered mitomycin alone at a dose of 6 mg/kg; mark "■" represents the group which was administered mitomycin alone at a dose of 3 mg/kg; mark "Δ" represents the group which was administered the monoclonal antibody jointly with mitomycin; and mark "○" represents the control group. The horizontal axis represents the number of days after the tumor inoculation. The longitudinal axis represents the tumor volume (mm$^3$).

FIG. 3 is a graph showing the changes in tumor volume when the VPF monoclonal antibody and mitomycin were used jointly. In this Fig., mark "●" represents the group which was administered the monoclonal antibody alone at a dose of 12.5 μg/mouse; mark "▲" represents the group which was administered mitomycin alone at a dose of 6 mg/kg; mark "◆" represents the group which was administered mitomycin alone at a dose of 3 mg/kg; mark "Δ" represents the group which was administered the monoclonal antibody jointly with mitomycin; and mark "○" represents the control group. The horizontal axis represents the number of days after the tumor inoculation. The longitudinal axis represents the tumor volume (mm³).

Figure 4:
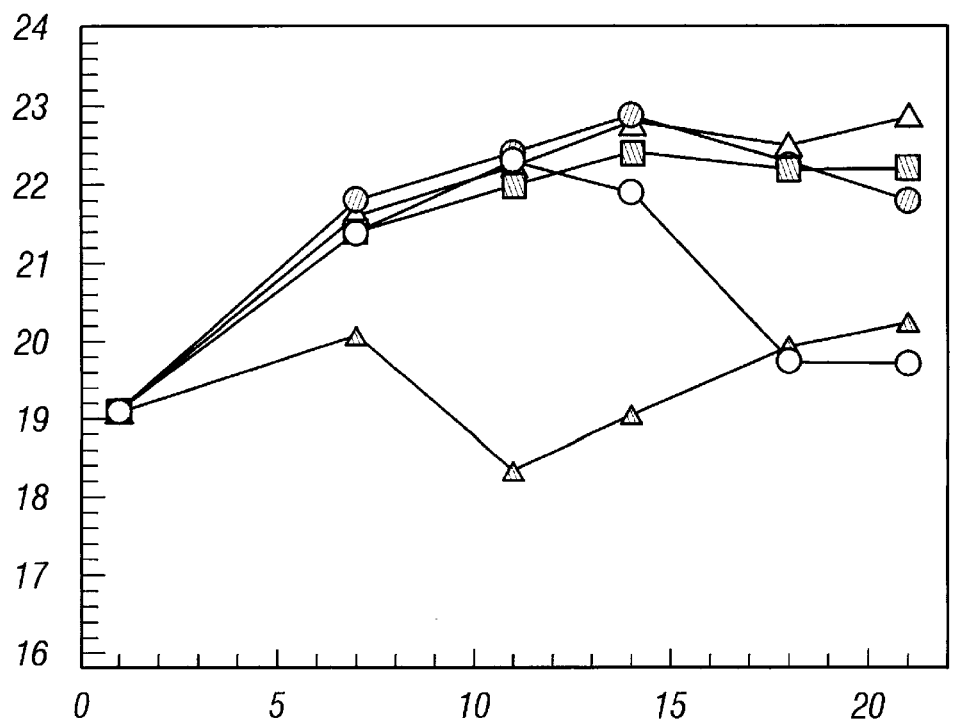
FIG. 4 is a graph showing the changes in tumor volume when the VPF monoclonal antibody and mitomycin were used jointly. In this Fig., each mark has the same meaning as in FIG. 3. The horizontal axis represents the number of days after the tumor inoculation. The longitudinal axis represents the changes in body weight (g).

FIG. 4 is a graph showing the changes in tumor volume when the VPF monoclonal antibody and mitomycin were used jointly. In this Fig., each mark has the same meaning as in FIG. 3. The horizontal axis represents the number of days after the tumor inoculation. The longitudinal axis represents the changes in body weight (g).

Figure 5:
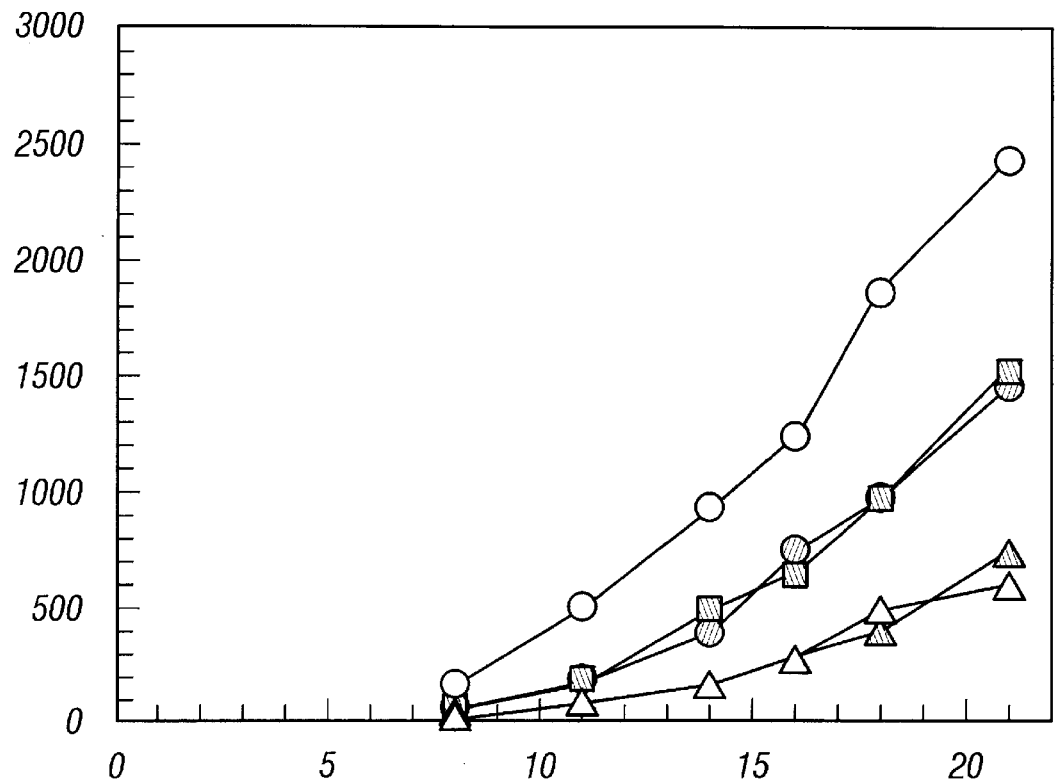
FIG. 5 is a graph showing the changes in tumor volume when the VPF monoclonal antibody and cisplatin were used jointly. In this Fig., mark "●" represents the group which was administered the monoclonal antibody alone at a dose of 12.5 μg/mouse; mark "▲" represents the group which was administered cisplatin alone at a dose of 10 mg/kg; mark "■" represents the group which was administered cisplatin alone at a dose of 5 mg/kg; mark "Δ" represents the group which was administered the monoclonal antibody jointly with cisplatin; and mark "○" represents the control group. The horizontal axis represents the number of days after the tumor inoculation. The longitudinal axis represents the tumor volume (mm$^3$).

FIG. 5 is a graph showing the changes in tumor volume when the VPF monoclonal antibody and cisplatin were used jointly. In this Fig., mark "●" represents the group which was administered the monoclonal antibody alone at a dose of 12.5 μg/mouse; mark "▲" represents the group which was administered cisplatin alone at a dose of 10 mg/kg; mark "■" represents the group which was administered cisplatin alone at a dose of 5 mg/kg; mark "Δ" represents the group which was administered the monoclonal antibody jointly with cisplatin; and mark "○" represents the control group. The horizontal axis represents the number of days after the tumor inoculation. The longitudinal axis represents the tumor volume (mm³).

Figure 6:
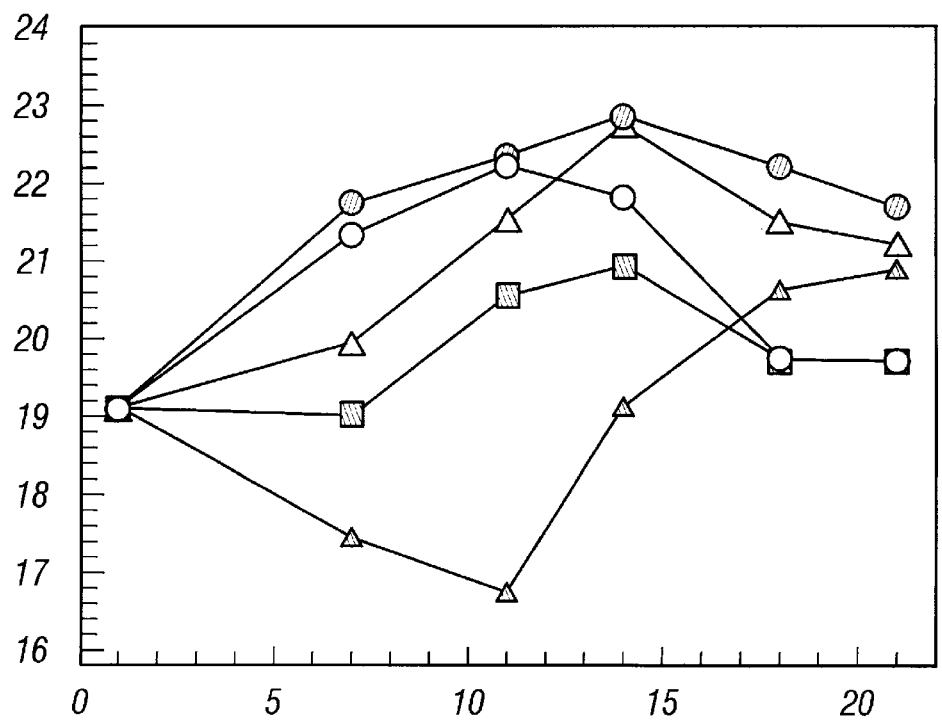
FIG. 6 is a graph showing the changes in tumor volume when the VPF monoclonal antibody and cisplatin were used jointly. In this Fig., each mark has the same meaning as in FIG. 5. The horizontal axis represents the number of days after the tumor inoculation. The longitudinal axis represents the changes in body weight (g).

FIG. 6 is a graph showing the changes in tumor volume when the VPF monoclonal antibody and cisplatin were used jointly. In this Fig., each mark has the same meaning as in FIG. 5. The horizontal axis represents the number of days after the tumor inoculation. The longitudinal axis represents the changes in body weight (g).

As is clear from these Figs., the group which was administered mitomycin jointly with VPF monoclonal antibody has exhibited a stronger antitumor activity than the groups which received mitomycin alone and the antibody alone, respectively. No loss in the body weight was observed in the joint use group. On the other hand, when mitomycin alone was administered at a dose of 6 mg/kg, a strong antitumor activity was observed but loss in body weight was also observed. With respect to cisplatin, similar results were obtained.

Effect of the Invention

According to the present invention, there are provided peptides of those portions which are important for tumor growth in VPF and monoclonal antibodies reactive with the peptides. The peptide of the invention is useful for the preparation of a monoclonal antibody having a strong antitumor activity against VPF and for biochemical analysis of the activity expression of VPF. The VPF monoclonal antibody of the invention reactive with the above peptide is useful as a reagent for biochemical analysis of VPF, and it is also applicable as a therapeutic agent for treating angiogenesis-associated diseases or as a suppressant against cancer growth.

What is claimed is:

1. A peptide having the amino acid sequence as shown in any one of SEQ ID NO: 1, SEQ ID NO: 2 or SEQ ID NO: 3.

2. A peptide having an amino acid sequence as set forth in SEQ ID NO:1.

3. A peptide having an amino acid sequence as set forth in SEQ ID NO:2.

4. A peptide having an amino acid sequence as set forth in SEQ ID NO:3.

5. A vascular endothelial cell growth factor (VPF) monoclonal antibody which binds to the peptide of claim 1.

6. A monoclonal antibody which binds to the peptide of claim 1, wherein the monoclonal antibody has an isoelectric point (pI) of 5.2–5.5.

7. A pharmaceutical composition comprising as an active ingredient the antibody of claim 5 or a fragment of the antibody of claim 5.

8. A pharmaceutical composition comprising as an active ingredient the antibody of claim 6 or a fragment of the antibody of claim 6.

9. A pharmaceutical composition comprising as an active ingredient a F(ab) or F(ab)'2 fragment of the antibody of claim 5.

10. A pharmaceutical composition comprising as an active ingredient a F(ab) or F(ab)'2 fragment of the antibody of claim 6.

11. A pharmaceutical composition comprising as an active ingredient:
   (i) the antibody of claim 5 bound to a toxin or a radioisotope;
   (ii) a fragment of the antibody of claim 5 and which is bound to a toxin or a radioisotope; or
   (iii) an F(ab) or F(ab)'$_2$ fragment of the antibody of claim 5 which fragment is bound to a toxin or a radioisotope.

12. A pharmaceutical composition comprising as an active ingredient:
   (i) the antibody of claim 6 bound to a toxin or a radioisotope;
   (ii) a fragments of the antibody of claim 6 and which is bound to a toxin or a radioisotope; or
   (iii) an F(ab) or F(ab)'$_2$ fragment of the antibody of claim 6 which fragment is bound to a toxin or a radioisotope.

13. A method for treating cancer comprising administering to a subject the antibody of claim 5 or a fragment of the antibody of claim 5.

14. A method for treating cancer comprising administering to a subject the antibody of claim 6 or a fragment of the antibody of claim 6.

15. A method for treating cancer comprising administering to a subject a F(ab) or F(ab)'$_2$ fragment of the antibody of claim 5.

16. A method for treating cancer comprising administering to a subject a F(ab) or F(ab)'$_2$ fragment of the antibody of claim 6.

17. A method for treating cancer comprising administering to a subject the antibody of claim 5 or a fragment of the antibody of claim 5 which is bound to a toxin or a radioisotope.

18. A method for treating cancer comprising administering to a subject the antibody of claim 6 or a fragment of the antibody of claim 6 which is bound to a toxin or a radioisotope.

19. A method for treating cancer comprising administering to a subject a F(ab) or F(ab)'$_2$ fragment of the antibody of claim 5 which fragment is bound to a toxin or a radioisotope.

20. A method for treating cancer comprising administering to a subject a F(ab) or F(ab)'$_2$ fragment of the antibody of claim 6 which fragment is bound to a toxin or a radioisotope.

21. A VPF monoclonal antibody MV833.

22. A pharmaceutical composition comprising as an active ingredient a vascular endothelial cell growth factor (VPF) monoclonal antibody which binds to a peptide of claim 1.

23. The pharmaceutical composition of claim 22, wherein the VPF monoclonal antibody is bound to a toxin or a radioisotope.

24. A method for treating cancer comprising administering to a subject a vascular endothelial cell growth factor (VPF) monoclonal antibody which binds to a peptide of claim 1.

25. The method of claim 24, wherein the VPF monoclonal antibody is bound to a toxin or a radioisotope.

* * * * *